US006883365B2

United States Patent
Fasanotti

(10) Patent No.: US 6,883,365 B2
(45) Date of Patent: Apr. 26, 2005

(54) FOCUSING DEVICE FOR VOLATILE AND SEMIVOLATILE ORGANIC COMPOUNDS IN THE GASEOUS PHASE

(75) Inventor: Umberto Saini Fasanotti, Breganzona (CH)

(73) Assignee: Dani Strumentazione Analitica S.p.A., Cologno Monzese (IT)

(*) Notice: Subject to any disclaimer, the term of this patent is extended or adjusted under 35 U.S.C. 154(b) by 0 days.

(21) Appl. No.: 10/380,166
(22) PCT Filed: Aug. 7, 2001
(86) PCT No.: PCT/EP01/09107
§ 371 (c)(1), (2), (4) Date: Mar. 18, 2003
(87) PCT Pub. No.: WO02/37097
PCT Pub. Date: May 10, 2002

(65) Prior Publication Data
US 2004/0093929 A1 May 20, 2004

(51) Int. Cl.⁷ ............................ G01N 1/00; G01N 30/02
(52) U.S. Cl. .................... 73/23.41; 73/23.41; 73/23.26; 73/23.22; 73/23.4; 73/25.03
(58) Field of Search .............................. 73/23.41, 23.26, 73/23.22, 23.4, 25.03

(56) References Cited

U.S. PATENT DOCUMENTS 3,057,183 A   10/1962  De Ford
5,929,321 A   7/1999   Bertrand

FOREIGN PATENT DOCUMENTS

WO   WO 98/21574   5/1998

Primary Examiner—Hezron Williams
Assistant Examiner—André K. Jackson
(74) Attorney, Agent, or Firm—Hoffman, Wasson & Gitler, PC

(57) ABSTRACT

A focusing device for volatile and semi-volatile organic compounds in the gaseous phase, comprising a support structure, a container for said organic compounds, a cooling element and a heating element for their transfer to the analysis system, characterized in that said cooling element and said heating element are positioned in two separate regions of said support structure and form a single block movable relative to said container.

9 Claims, 2 Drawing Sheets

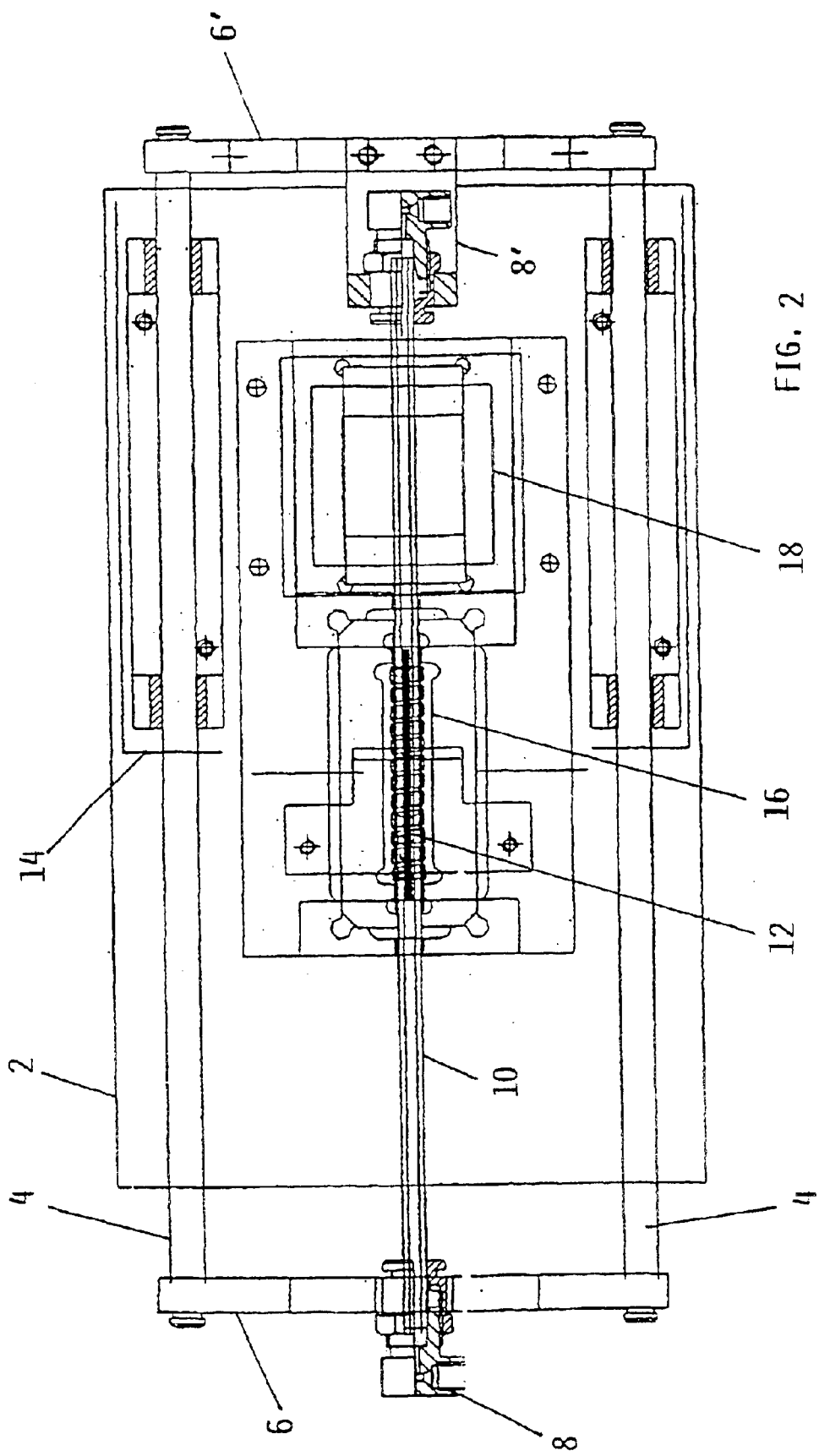

Figure 1:
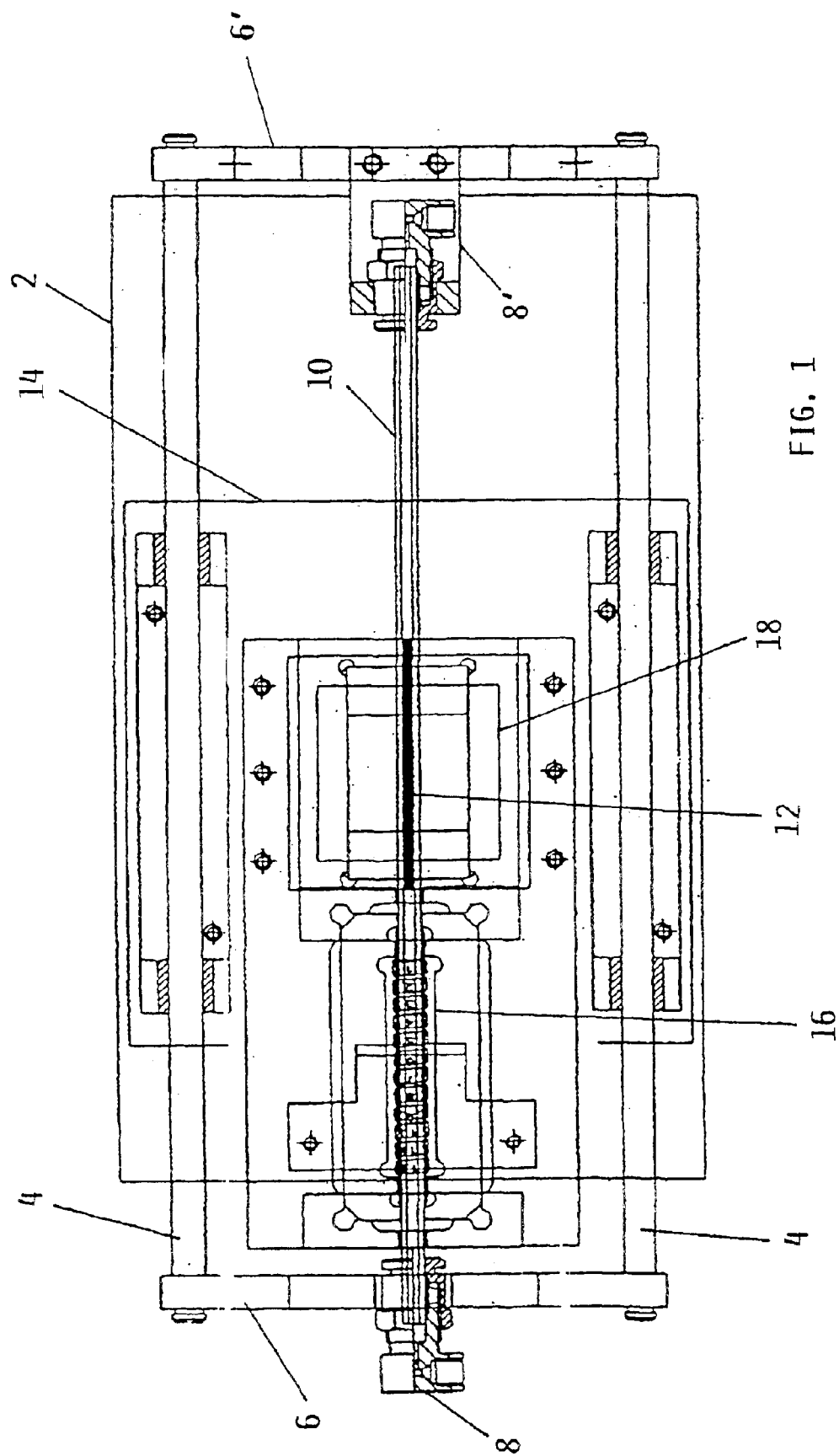

FOCUSING DEVICE FOR VOLATILE AND SEMIVOLATILE ORGANIC COMPOUNDS IN THE GASEOUS PHASE

This invention relates to a focusing device for volatile and semivolatile organic compounds in the gaseous phase.

Focusing traps used in analytical instrumentation, in particular for gas chromatography, are known for concentrating the volatile and semi-volatile compounds present in a gaseous phase, before transferring them to an analysis system.

Said organic compounds are concentrated by cooling the focusing trap, and are transferred to the analysis system by heating the trap.

With known focusing traps, during their operation the heating system and cooling system are in a fixed position relative to the trap, which can be heated only on termination of the preceding cooling stage.

A drawback of known focusing traps is that their applicational performance, which is greater the faster the passage from low temperature (concentration stage) to high temperature (transfer stage), is limited by the limited trap heating rate, related to the rate of temperature rise of the heater, which has to start from cold and hence requires several seconds to reach and stabilize itself at the predetermined temperature.

Another drawback is the possible presence of interactions between the heating element and the cooling element.

A preferred embodiment of the invention is described in detail hereinafter with references to the accompanying drawings, in which:

FIG. 1 is a schematic view of the focusing device of the invention in the cooling condition, and FIG. 2 shows it in the heating condition.

As can be seen from the figures, the device of the invention comprises a support structure 2 provided with parallel columns 4, supported at their ends by two plates 6, 6'.

By means of suitable connectors 8, 8', the two plates 6, 6' support a tube 10, the central portion 12 of which constitutes the "trap" for the organic compounds to be analyzed.

In the interior of the structure 2 there is provided, slidable along the columns 4, a block 14, to which an electric heater 16 and an electric cooler 18 are applied.

Said block 14 is driven to and for along the columns 4 by a connecting rod and crank system, which does not form part of the invention and is simply cited herein without being shown in the drawings.

The position of the heater 16 and of the cooler 18 relative to the block 14 is such that in one of the end positions the trap 12 is surrounded by the cooler 18, whereas in the other it is surrounded by the heater 16.

The device of the invention operates as follows:
initially, the block 14 is disposed such that the cooler 18 surrounds the trap 12 (see FIG. 1) and can cool the organic compounds contained within it, to condense them. At the same time, the heater 16, which is also powered so as to have already attained the predetermined working temperature, is laterally displaced from the trap 12.

When the trap has been cooled on the basis of the scheduled working cycle, the block 14 is slid along the columns 4 so that the heater 16 faces the trap 12 (see Fig 2). The heater which is already at its working temperature, heats the organic compounds contained in the trap with the necessary rapidity.

On termination of this stage, the heated organic compounds are transferred to the gas chromatograph.

From the foregoing description, it is apparent that, as the trap passes from the cooling stage to the heating stage, not statically by electrically activating/deactivating the two elements 16, 18 provided for this purpose, but instead dynamically by moving these latter, which are always maintained at their working temperature, the trap is able to attain the predetermined operating conditions more rapidly. In particular, heating of the trap 12 is faster, especially during the initial stage immediately after the cooling stage, because when the trap comes face to face with the heater, this component is already thermally stabilized at the set temperature.

By virtue of this rapid heating, transfer to the analysis system is more effective and rapid.

Moreover, with the device of the instant invention, there is no thermal interaction between the heating element and the cooling element which are spaced apart along block 14.

What is claimed is:

1. A focusing device for volatile and semi-volatile organic compounds in the gaseous phase, said focusing device comprising:

a) a container consisting of a tubular elements, the central portion of which receives organic compounds to be analyzed;

b) a block movable relative to said container;

c) a cooling element situated proximate to said container for concentrating said organic compounds, the length of said cooling element being substantially equal to the axial length of said central portion;

d) a heating element situated proximate to said container for transferring said organic compounds from said focusing device to a gas analysis system, the length of said heating element being substantially equal to the axial length of said central portion;

e) said cooling element and said heating element being secured to two axially separated regions on said block so that there is no thermal interaction between said elements;

f) a support structure including spaced first means at opposite sides thereof for supporting the opposite ends of said container;

g) said support structure further including second means for supporting said block for movement relative to said container;

h) said block movable along said second means for supporting same between two extreme positions;

i) said block, in one extreme position, positioning said cooling element in operative relation to said central portion of said container and said heating element in non-operative relation to said central portion; and j) said block, in its other extreme position, positioning said heating element in operative relation to said central portion of said container and said cooling element in non-operative relation to said central portion.

2. A focusing device as claimed in claim 1 wherein said spaced first means comprises a pair of lateral plates, one plate at each end of said support structure, and a first connector secured to one plate, and a second connector to the other plate, the connectors receiving the opposite end of said container.

3. A focusing device as claimed in claim 2 wherein said second means for supporting said block for movement relative to said container comprises a plurality of parallel columns that extend along the longitudinal extent of said support structure, said parallel columns being supported by said pair of lateral plates, said block being movable along said columns between the extreme positions.

4. A focusing device as claimed in claim 1 wherein said heating element and said cooling element are shaped to surround said container.

5. A focusing device as claimed in claim 1 further including electrical means for activating said cooling means and said heating means, said cooling means and said heating means always being maintained at their working temperatures.

6. A focusing device for volatile and semi-volatile organic compounds in the gaseous phase, said focusing device comprising:
   a) a container consisting of an elongated tubular duct, the central portion of which is adapted to receive organic compounds to be analyzed;
   b) a support structure including first, axially spaced means for supporting the opposite ends of said container;
   c) a cooling element situated proximate to said container for concentrating the organic compounds, the length of said cooling element being substantially equal to the axial dimension of the central portion of said container;
   d) a heating element situated proximate to said container for transferring the organic compounds from said focusing device to a gas analysis system, the length of said heating element being substantially equal to the axial dimension of the central portion of said container;
   e) a block movable relative to said container in the axial direction;
   f) said cooling element and said heating element secured to two separate spaced apart regions on said block so that there is no thermal interaction between said heating and cooling elements;
   g) said support structure further including second means for supporting said block for movement relative to said container;
   h) said block being movable along said second means for supporting same, in an axial direction, between two extreme positions;
   i) said block, in one extreme position, positioning said cooling element in operative relation to said central portion of said container and said heating element in non-operative relation to said central portion; and
   j) said block, in its other extreme position, positioning said heating element in operative relation to said central portion of said container and said cooling element in non-operative relation to said central portion.

7. A focusing device, as claimed in claim 6, wherein said cooling element surrounds said container, and said heating element surrounds said container.

8. A focusing device, as claimed in claims 6, wherein said first, axially spaced means comprises a first and a second plate, said plates situated at opposite axial ends of said focusing device, a first connector secured to said first plate for supporting one end of said container, and a second connector secured to said second plate for supporting the other end of said container.

9. A focusing device, as claimed in claim 8, wherein said means for supporting said block comprises parallel columns extending between said first and second plates, said block being supported by, and slidable along, said parallel columns.

* * * * *